United States Patent [19]

Verma et al.

[11] Patent Number: 5,449,446
[45] Date of Patent: Sep. 12, 1995

[54] MULTI-PURPOSE ELECTROPHORESIS APPARATUS

[76] Inventors: Sumeet Verma; Kuldeep Verma, both of 3509 Crofton Ct., Raleigh, N.C. 27604

[21] Appl. No.: 208,604

[22] Filed: Mar. 9, 1994

[51] Int. Cl.[6] .................. G01N 27/26; G01N 27/447
[52] U.S. Cl. ................................ 204/301; 204/182.8; 204/299 R
[58] Field of Search ................ 204/299 R, 301, 182.8

[56] References Cited

U.S. PATENT DOCUMENTS

| | | | |
|---|---|---|---|
| 4,657,655 | 4/1987 | Smoot et al. | 204/299 R |
| 4,726,889 | 2/1988 | Love et al. | 204/182.8 |
| 4,830,725 | 5/1989 | Berninger et al. | 204/299 R |
| 4,840,714 | 6/1989 | Littlehales | 204/182.8 X |
| 4,889,606 | 12/1989 | Dyson et al. | 204/182.8 |
| 4,911,816 | 3/1990 | Love et al. | 204/299 R |
| 4,994,166 | 2/1991 | Fernwood et al. | 204/299 R |
| 5,013,420 | 5/1991 | Schuette | 204/299 R |
| 5,102,518 | 4/1992 | Doering et al. | 204/180.1 |
| 5,102,524 | 4/1992 | Dutertre | 204/299 R |
| 5,112,459 | 5/1992 | Sorge et al. | 204/180.1 |
| 5,137,613 | 8/1992 | Brumley, Jr. et al. | 204/299 R |
| 5,217,592 | 6/1993 | Jones | 204/299 R |
| 5,234,559 | 8/1993 | Collier et al. | 204/182.8 |
| 5,279,721 | 1/1994 | Schmid | 204/182.8 |

OTHER PUBLICATIONS

Fisher Scientific Company catalog, pp. 122 and 126.
Life Technologies Company catalog, pp. 445, 446, 449–458 and 461–472.
Copy of technical article, "The Bidirectional Transfer of DNA and RNA to Nitrocellulose or Diazobenzyloxymethyl-Paper", Gale E. Smith and Max D. Summers, 1980.

Primary Examiner—John Niebling
Assistant Examiner—John S. Starsiak, Jr.
Attorney, Agent, or Firm—Olive & Olive

[57] ABSTRACT

The invention disclosed herein comprises a laboratory electrophoresis apparatus which overcomes many drawbacks of the previously known apparatus by combining a number of operations in the same unit, thereby eliminating the need for moving a gel between analytic jobs. The apparatus of the invention has a gel casting platform permanently mounted in a buffer container with retractable dams on two opposite sides to retain the gel casting liquid prior to solidification. The gel remains in place on the platform and the dams are retracted for filling the buffer container and a vertical electric field is applied to compact the sample placed in the sample wells to the bottom. The electrophoresis in a horizontal direction is performed and may be observed by means of an included UV radiation source capable of causing the ethidium bromide treated molecular samples to emit visible light, which is observable through a UV opaque safety cover. A viewing hood including a UV cross-linking source may be substituted for viewing, especially during blotting or eluting operations, for which the gel is not moved from its casting platform. To do blotting, either a complete transfer membrane or a partial, single band membrane with a novel holder is used. A further operation is performed by the replacement of the viewing hood with a photography hood for the placement of a camera, capable of either UV or visible light photography. By this combination of features, the multi-purpose apparatus of the invention permits all necessary molecular analytic operations without the movement of the gel, thus improving the efficiency and reliability of results.

24 Claims, 14 Drawing Sheets

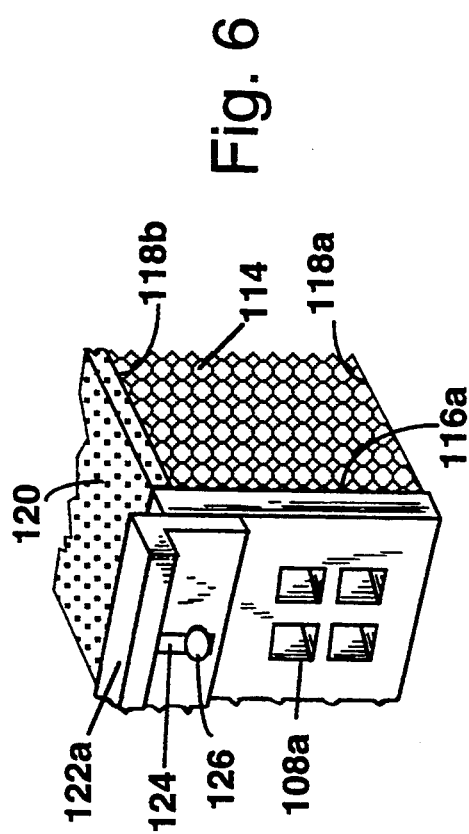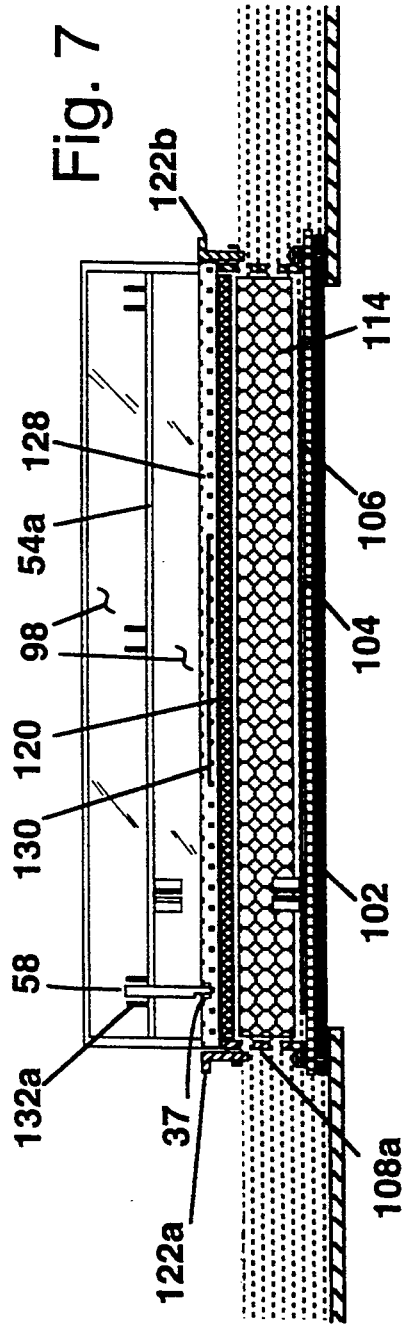

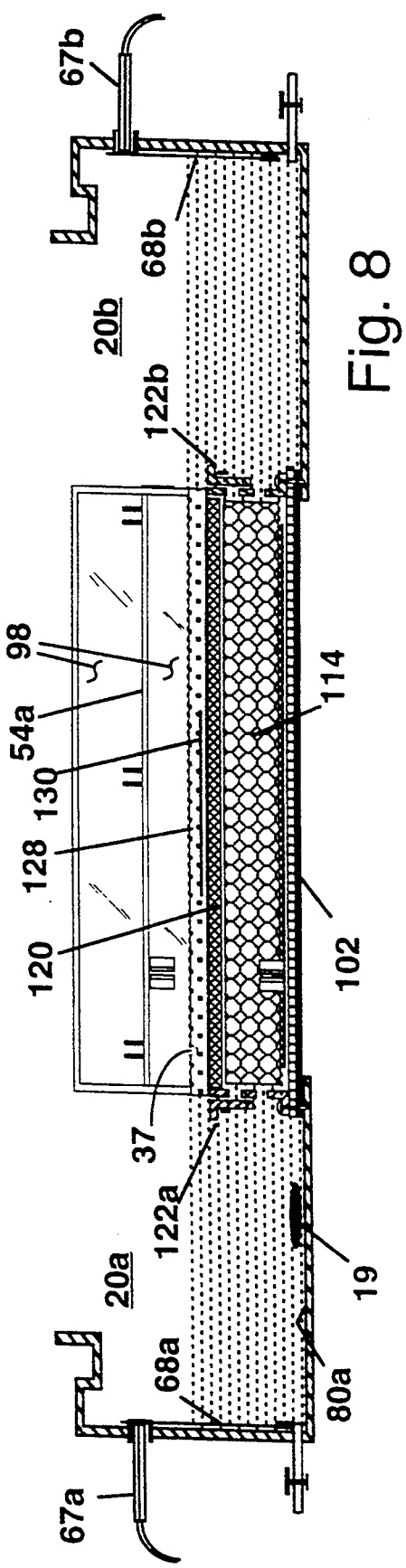
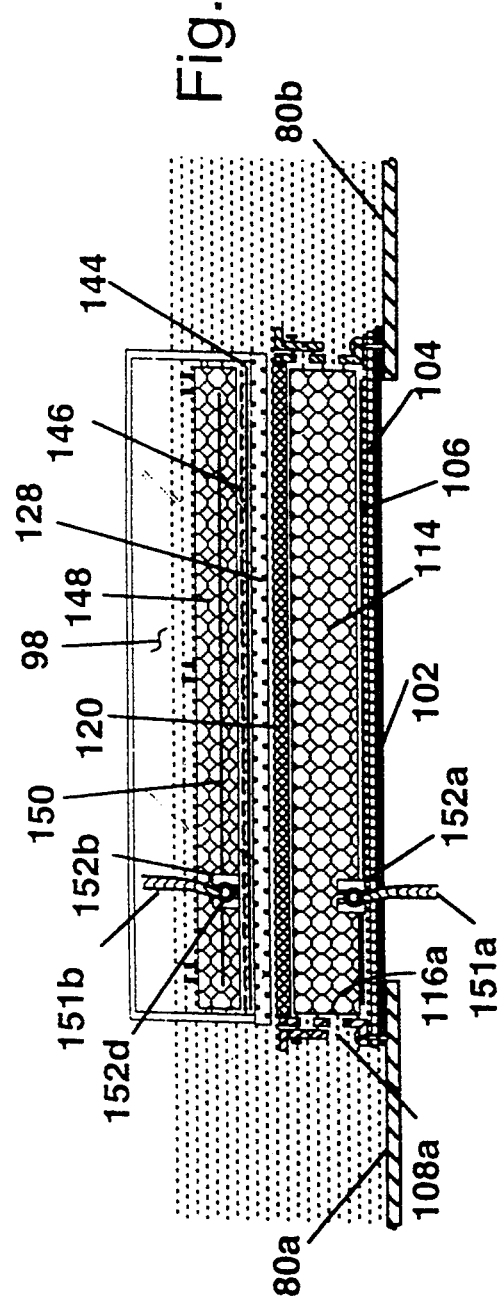
Fig. 8
Fig. 9

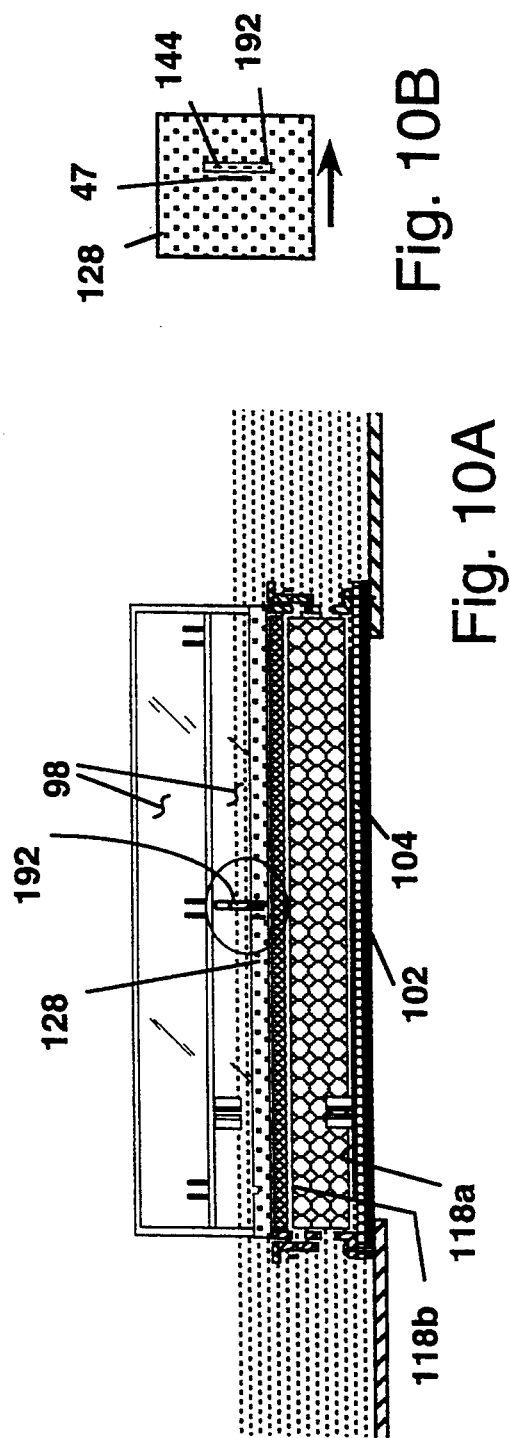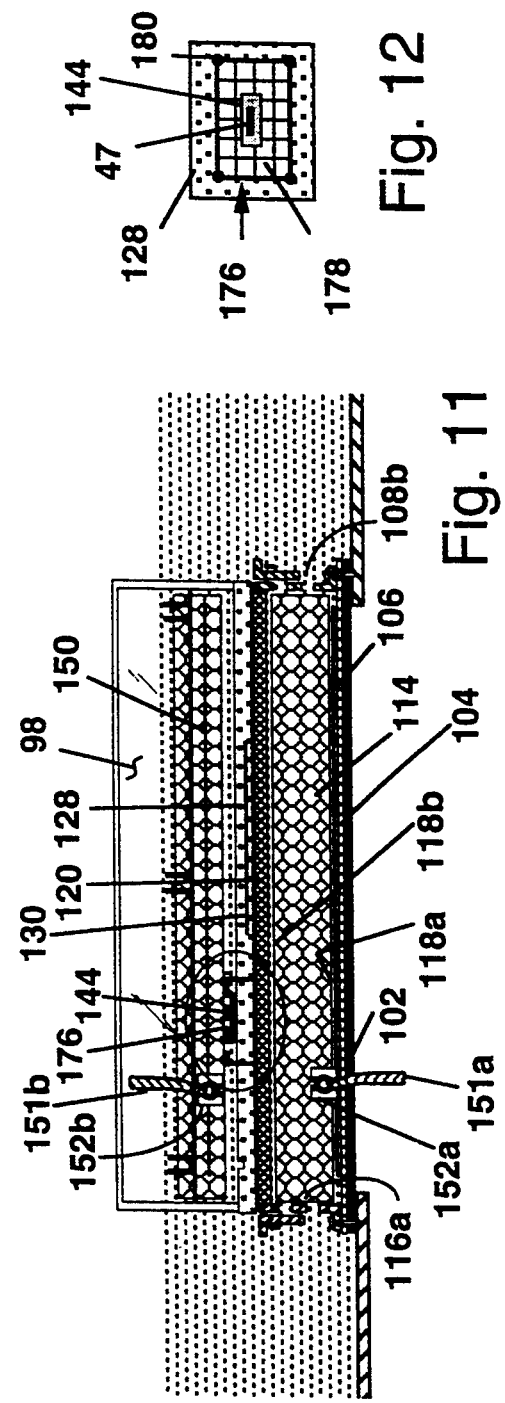

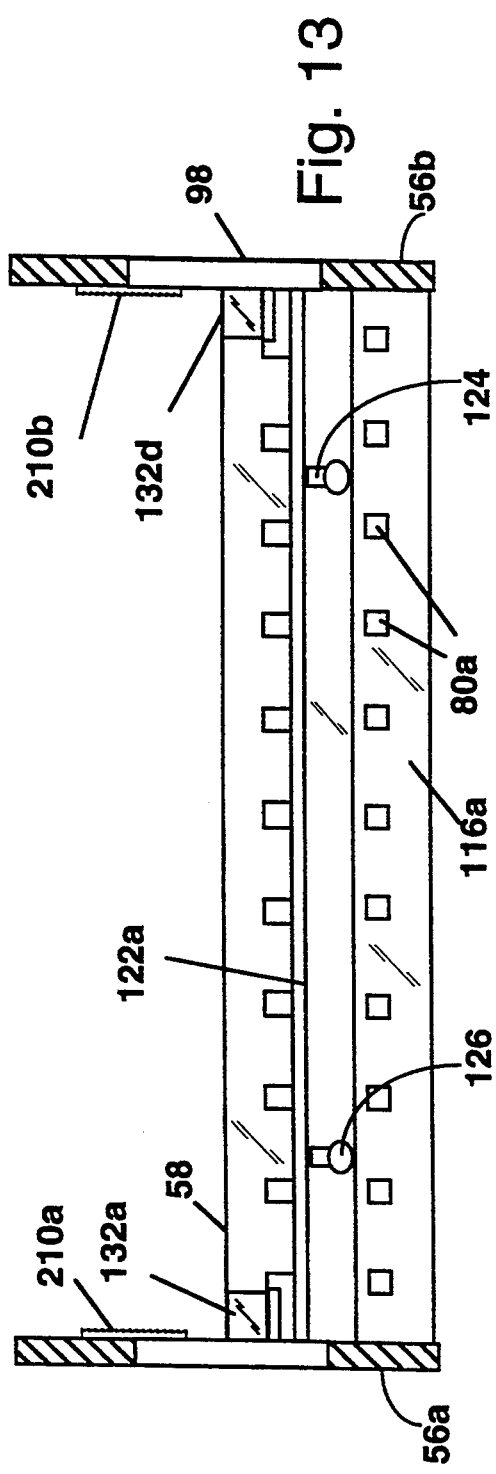
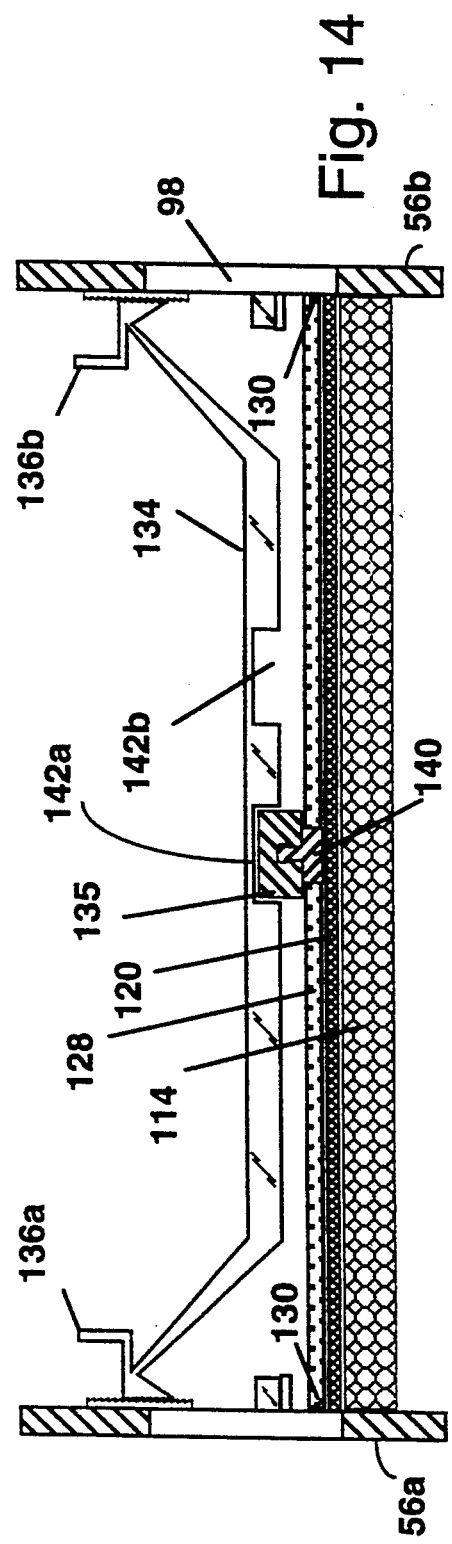

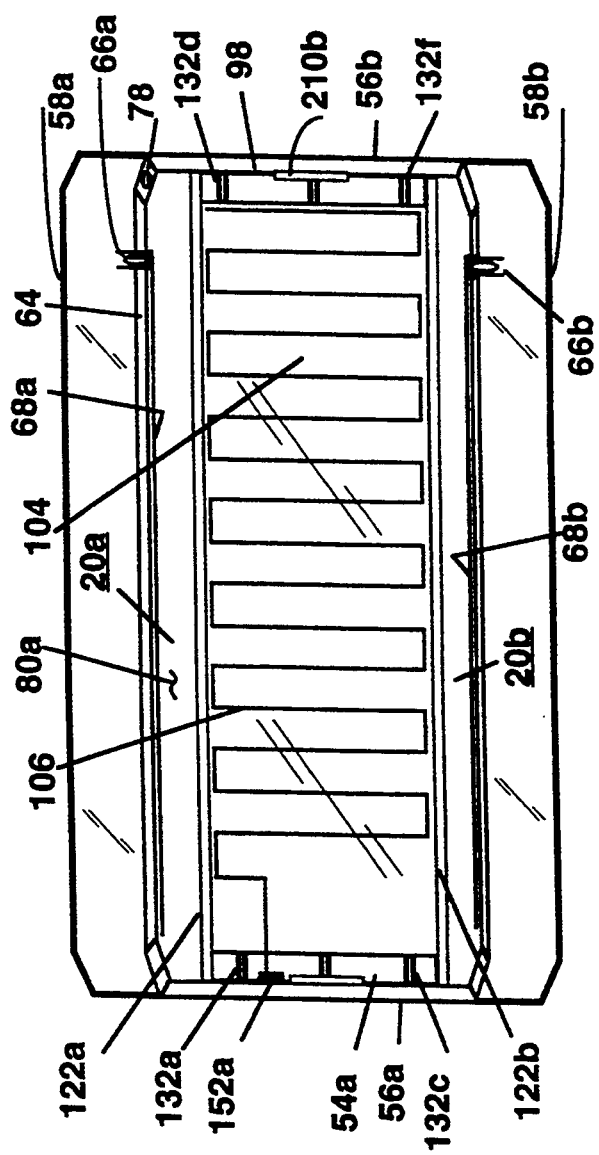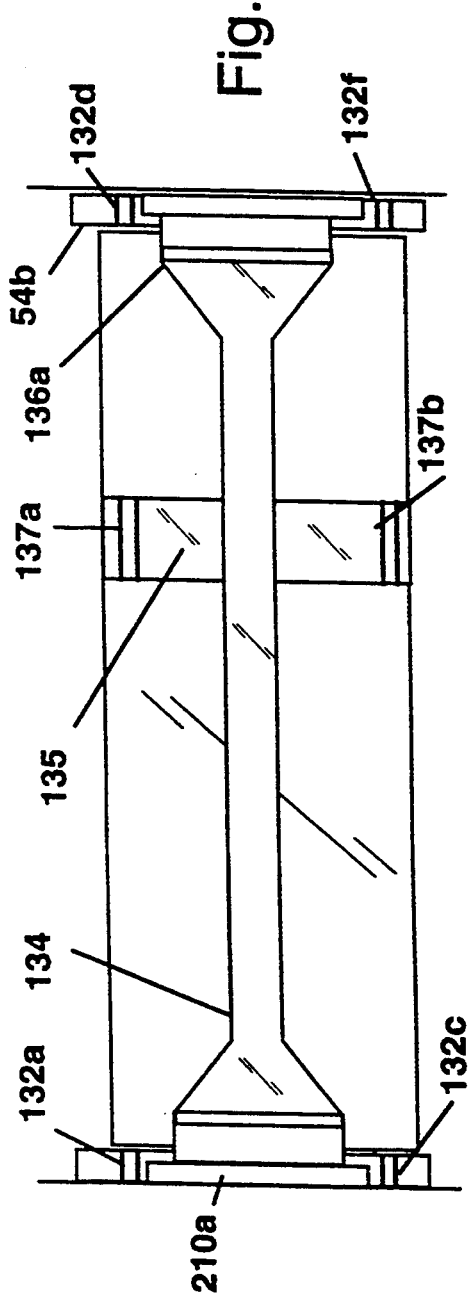

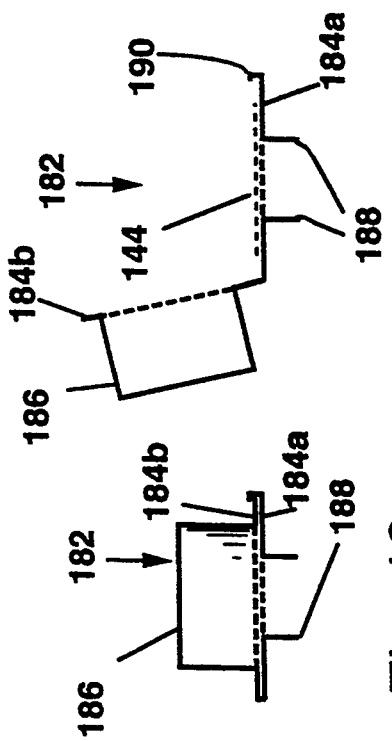
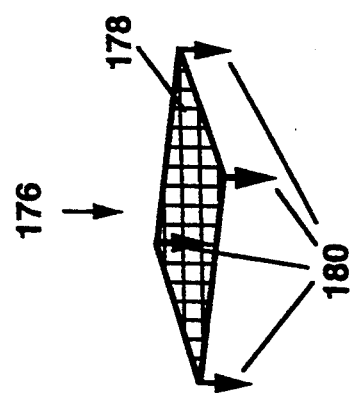
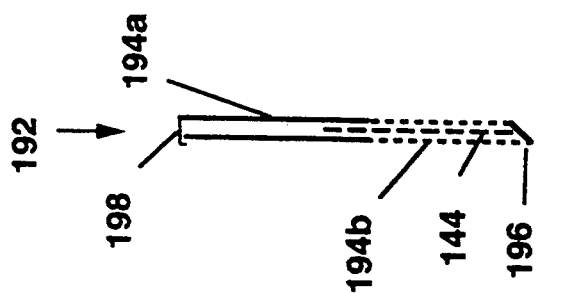
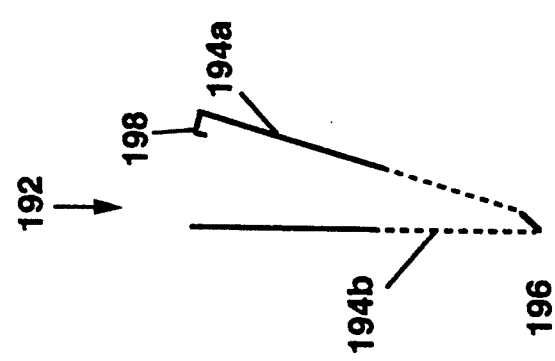

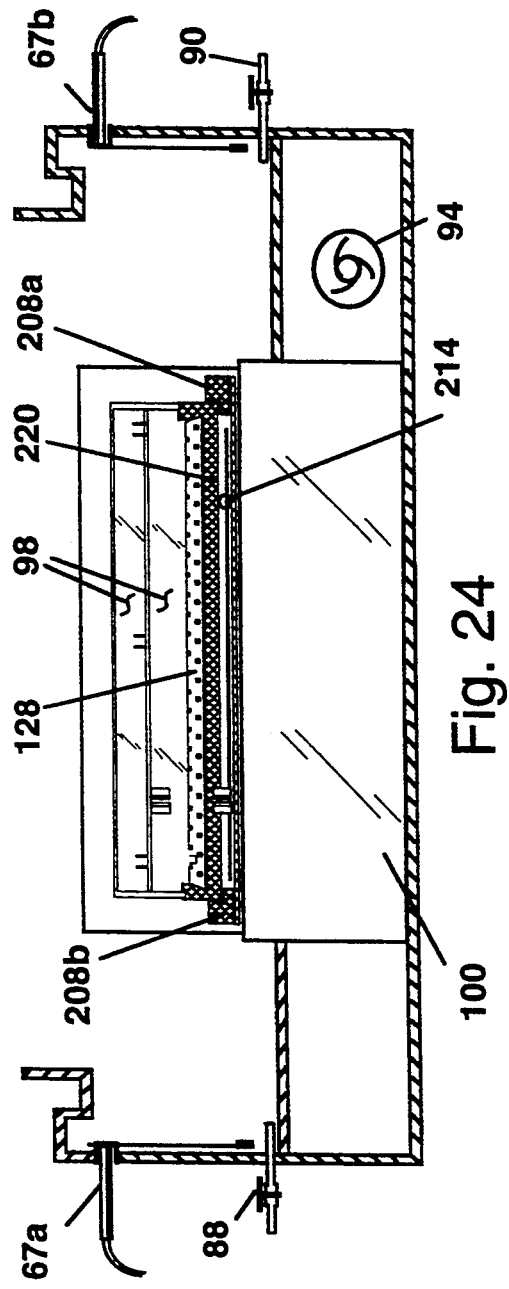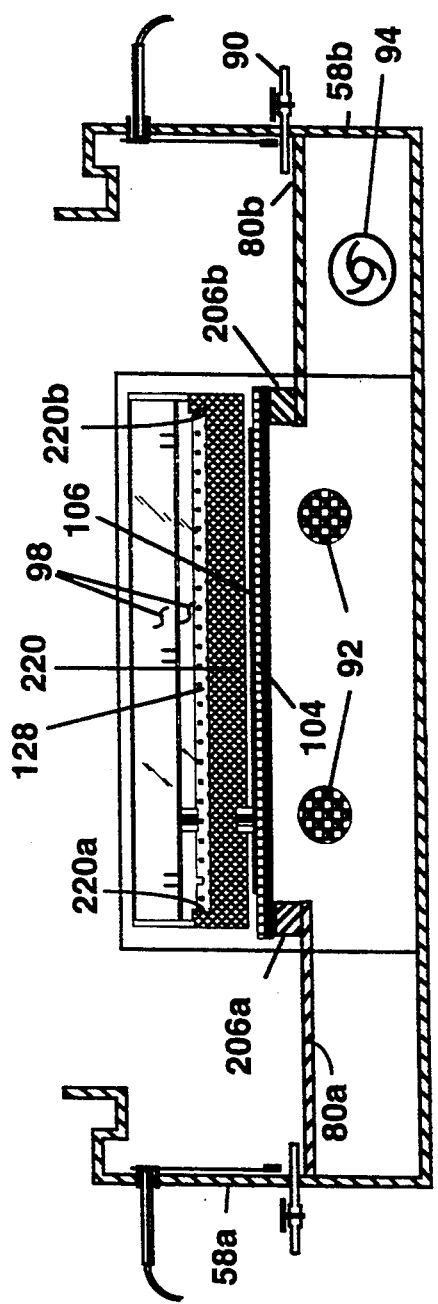

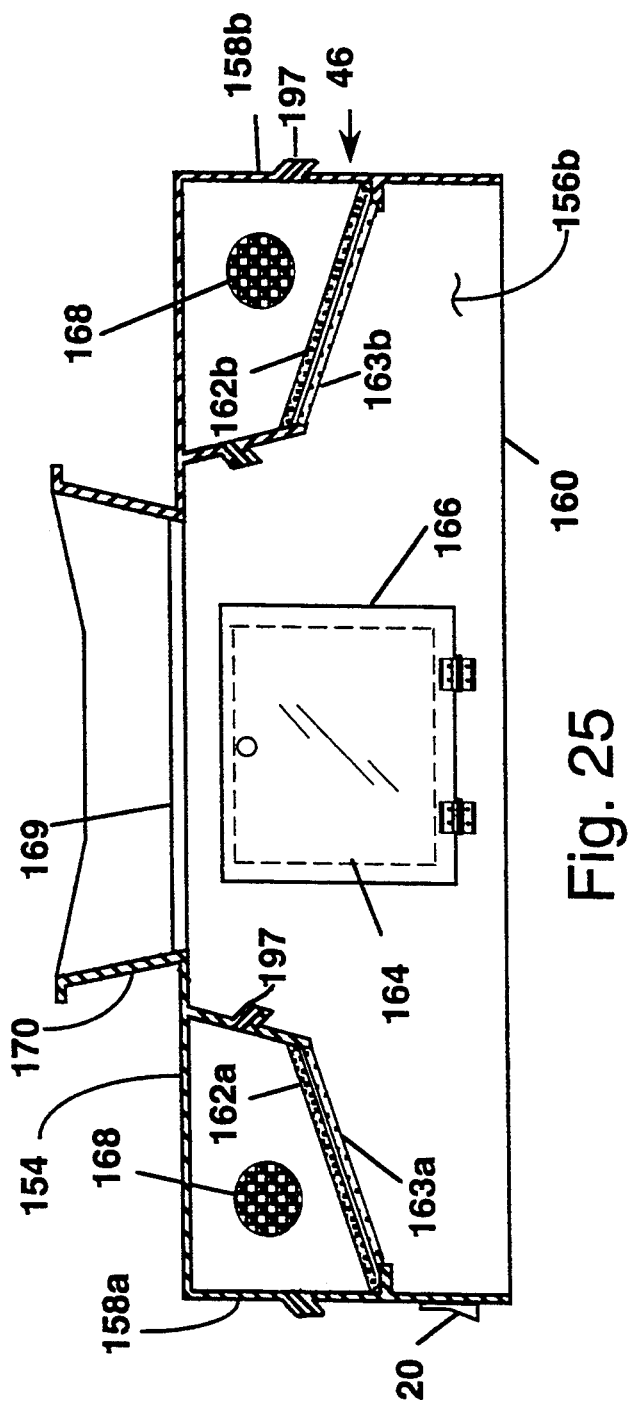
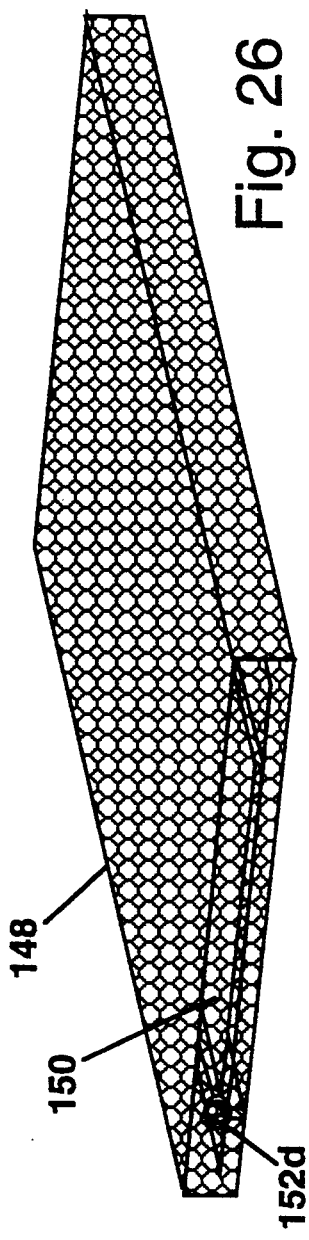

MULTI-PURPOSE ELECTROPHORESIS APPARATUS

BACKGROUND OF THE INVENTION

1. Field of the Invention

The invention disclosed relates to a multi-purpose laboratory apparatus, in particular a single, multi-purpose, apparatus in which electrophoresis, horizontal and vertical electroblotting and/or electroelution, vacuum blotting, capillary blotting, UV observation of ethidium bromide labeled specimens, UV photography and UV cross linking may each be performed. Additional feature includes buffer circulation, light opaque enclosure, DNA band compaction and DNA elution without cutting DNA band.

2. Description of the Related Art

Gel electrophoresis is a key analytical tool in molecular biology and clinical sciences. The electrophoresis of DNA and other organic molecules accomplished under the influence of an electric field is known. In order to perform this process, a semisolid gel of agarose, polyacrylamide or other similar castable, transparent material, is cast in a mold to produce a thin rectangular slab. Wells, or depressions, are formed in the upper surface of the slab along a line positioned at one end or in the center of the gel slab. The entire gel slab is then placed in a chamber having electrodes at each end. The chamber is then filled with a buffer solution to a level higher than the gel. Selected wells are filled with a solution containing the sample being analyzed, and a high gradient electric field is applied to the gel through the buffer solution. The molecules comprising the samples are caused to separate into sample bands by migrating through the gel slab towards the oppositely charged electrode at different rates depending upon their mobility, a function of molecular charge density and molecular size.

Gels are fragile. Manipulation can often cause a gel to rip or distort, possibly resulting in lost or unreliable experimental results. For example, the sample is typically stained with an intercalating fluorescent reagent e.g. ethidium bromide, which gives the DNA band sharp fluorescence under UV irradiation. An operator using currently known electrophoresis equipment cannot observe ethidium bromide stained DNA sample band migration during electrophoresis or electroblotting. Traditionally, the operator must terminate electrophoresis and transport the gel to a sample evaluation transilluminator utilizing a UV light source to irradiate ethidium bromide stained DNA for visual inspection of sample separation. If additional electrophoresis is required to complete the test, the gel must be returned to the chamber and the process resumed. Subsequently, to obtain a permanent record of the sample separation results, the DNA gel must again be physically transported from the electrophoretic device to a UV transilluminating platform above which the operator mounts a UV sensitive camera for photographing the gel. An inexperienced operator often wastes a number of film exposures during the process of aligning a gel slab on a UV platform before obtaining a good photograph. As stated above, these frequent manipulations can compromise gel integrity and lead to lost or unreliable research data. In addition, when the gel is reinserted into the electrophoresis chamber after observation, a change from the original gel position, or from the original buffer pH, temperature or composition may complete the electrophoretic run under different operating conditions, and possibly lead to further unreliable research data.

The usefulness of electrophoresis depends on producing thin, well defined molecular sample bands. This definition depends, in part, on the manner in which the molecular sample migrates from the sample well along the gel. The sample well, the distribution of sample molecular material in the well, and the electric field all influence band definition. A molecular sample once deposited in a well migrates horizontally through the gel as a vertically oriented rectangle. The sides of the sample rectangle tend to migrate slower than the central portion, resulting in a U-shaped dispersed band. However, a macromolecular sample deposited in the front corner of the well migrates horizontally as a compact line through a comparatively small volume of gel, thus resulting in narrow, straight, well defined bands. Traditionally, an operator must use extreme care in loading of the sample to attempt to obtain a well defined band. However, despite such care, electrophoretic results are often diminished by the presence of U-shaped dispersed macromolecular sample bands.

Subsequent to electrophoresis, it is common to transfer the molecular sample bands from the gel to a suitable membrane for further purification, processing or analysis. This transfer process is generally known as electroblotting. A vertically or horizontally oriented high gradient electric field is applied to the gel to accomplish transfer of sample bands to an adjacent membrane. Particular transfer techniques, e.g. northern and southern blotting, typically employ nitrocellulose or nylon membranes. The adhered sample may then be hybridized to a probe for further analysis or processing. Electroelution, is a technique which typically employs Di-Ethyl Amino Ethyl Cellulose (DEAE cellulose) paper membrane. DEAE cellulose paper adsorbs sample bands which may then be recovered from the DEAE cellulose paper for further processing like washing and eluting with various solutions. Vacuum blotting is another method for transfer of a molecular sample from the gel to an adjacent membrane. Vacuum blotting is accomplished by exposing the gel to a mild vacuum to cause transfer of molecular sample from the gel to an adjacent membrane. Existing electrophoresis units are not equipped to handle vacuum blotting. Therefore, the gel must be transported, according to current methodology, from the electrophoresis unit to another device.

Capillary blotting is similar to the electro-blotting methods described above, except that transfer of DNA from the gel to an adjacent membrane is accomplished by capillary movement of a buffer in a direction from the gel towards the adjacent membrane, causing the transfer of DNA from the gel to an adjacent membrane. Existing electrophoresis units are not equipped to handle capillary blotting processes. Therefore, the gel must be transported, according to current methodology, from the electrophoresis unit to another device.

UV cross linking of DNA molecules is a process whereby DNA molecules which have been transferred to a nitrocellulose or nylon membrane are made to chemically bond to the nitrocellulose or nylon molecules in the membrane by exposure to UV radiation. Traditionally, for this bonding process, another separate piece of laboratory apparatus must be used.

All the above-mentioned electroblotting techniques require that the gel be removed from the electrophoresis device and deposited in a denaturation and neutralization bath before transfer. After bathing, the gel is deposited upon an electro-blot membrane. The membrane and gel are then sandwiched between absorbent layers and transferred to a separate electro-blot device for electro-transfer.

One device, taught by Shuette in U.S. Pat. No. 5,013,1820, consolidates electrophoresis and electroblotting. However, the gel must still be removed from the Shuette device after electrophoresis for denaturation and assembly of the sandwich. The sandwich is then reinserted into the Shuette device before electroblotting. Although the Shuette device consolidates electrophoresis and electroblotting procedures, the number of manipulation steps necessary to accomplish electro-transfer and which are required to take place outside the apparatus remain the same as in separate apparatus.

A second device, disclosed in U.S. Pat. No. 4,657,655 to Smoot et al., utilizes a gel-casting tray which may be mounted either in an electrophoresis chamber for separation processes or in a transilluminator for visualization and photography. The tray has vertically slidable side gates to go from a casting position to a lower position to locate the tray in each respective unit.

No single work station exists in which essentially all the above mentioned experimental procedures, can be performed. Laboratories must purchase various separate units, thus increasing cost and space requirements. Traditional techniques involving gel transfer also repeatedly expose operators to a known carcinogen, ethidium bromide.

Therefore, it is an object of the present invention to provide an apparatus which consolidates single or multiple gel electrophoresis, whole gel or single band electroeluting, electroblotting, capillary blotting, vacuum blotting, UV cross linking, UV observation, mini dark room and UV photography into one multipurpose work station.

Another object of the invention is to reduce handling and movement of the gel, reduce operator exposure to ethidium bromide and improve test result reliability.

Another object of the invention is to provide an apparatus to carry out horizontal as well as vertical movement of sample molecules without touching the gel.

It is a further object of the present invention to provide a universal work station apparatus that enables a molecular sample to be compressed to the front lower corner of each formed well for improved definition of molecular sample bands.

Another object of the invention is to provide a design in which the buffer solution is circulated.

Still another object of the present invention is to provide an apparatus for observation of molecular movement for complete electroblotting or electroelution which can be performed safely during UV operation.

Further objectives of the invention will become apparent from the description that follows.

SUMMARY OF THE INVENTION

The invention provides a single integrated apparatus capable of executing molecular separation in a gel and subsequent molecular transfer to a suitable membrane and for photographing the results. The apparatus of the invention includes a power source, an electrophoresis-electroblot-transilluminator unit, a viewing hood, a camera hood, an integral UV radiation source for sample detection and an integral UV radiation source for cross-linking.

The electrophoresis-electroblot-transilluminator unit, referred to above, is capable of horizontal separation of sample molecules within a gel and the subsequent vertical or horizontal transfer of the sample molecules to an adjacent membrane by electroblotting, capillary blotting or vacuum blotting techniques. The UV radiation source irradiates the gel to cause fluorescence of the molecular sample contained within. An UV filter window is made integral with the electrophoresis-electroblot-transilluminatorting unit and enables safe observation of the UV irradiated gel during the separation of the molecular sample within the gel and subsequent transfer of the molecular sample to an adjacent membrane. The cross-linking UV radiation source performs UV cross-linking of the separated molecular sample to the membrane. Membrane holders are provided for single molecular sample band or multiple molecular sample band electroelution or electroblotting. A viewing hood includes a service door through which forceps are used to place a membrane holder adjacent a selected molecular sample band. The UV filter viewing window referred to above in addition to its other functions also provides means for safely observing placement of the membrane adjacent to the selected molecular sample band.

BRIEF DESCRIPTION OF THEE DRAWINGS

FIG. 6 is a perspective view of a portion of the electrophoresis-electroblot-transilluminator unit with a slidable dam shown in its upper position.

FIG. 7 is a front elevation schematic view of the upper chamber of the electrophoresis-electroblot-transilluminator unit of FIG. 1 in its gel casting mode.

FIG. 8 is a front elevation schematic view of the upper chamber of the electrophoresis-electroblot-transilluminator unit of FIG. 1 in its horizontal electrophoresis mode.

FIG. 9 is a front elevation view of the upper chamber of FIG. 5 in its whole gel upward electroblotting mode.

FIG. 10A is a front elevation view of the upper chamber of the unit of FIG. 5 showing placement of a vertical membrane holder (in circle) inserted into a sample gel for single band horizontal electroelution.

FIG. 10B is a detailed top view of the vertical membrane holder shown in the circle of FIG. 10A.

FIG. 11 is a front elevation schematic view of the upper chamber of the unit of FIG. 5 showing placement of a mesh grid membrane holder (in circle) for single band vertical electroblotting.

FIG. 12 is a detailed top view of the mesh grid membrane holder shown in the circle of FIG. 11.

FIG. 13 is a side elevation schematic view of the upper chamber of the electrophoresis-electroblot-transilluminator unit of FIG. 5 showing a comb inserted to form wells when a gel is cast.

FIG. 14 is a side elevation schematic view of the upper chamber of the electrophoresis-electroblot-transilluminator unit showing a gel partition inserted therein so as to prepare two equal size gels.

FIG. 15 is a top plan schematic view of tile electrophoresis-electroblot-transilluminator unit showing electrodes mounted on a UV protector glass.

FIG. 16 is a top plan schematic view of tile electrophoresis-electroblot-transilluminator unit showing the gel partition positioned so as to prepare two unequal gels.

FIG. 17 is a perspective view of a mesh ,grid for holding a single band vertical blotting membrane.

FIG. 18 is a side elevation view of a hingeable single band vertical blotting membrane holder shown in its closed position.

FIG. 19 is a side elevation view of the hingeable membrane holder of FIG. 18 shown in its open position.

FIG. 20 is a side elevation view of a hingeable single band horizontal electroblotting membrane holder in its open position.

FIG. 21 is a side elevation view of the hingeable membrane holder of FIG. 20 in its closed position.

FIG. 24 is a front elevation schematic view of the electrophoresis-electroblot-transilluminator unit showing a further embodiment with fixed dams.

FIG. 25 is a side elevation schematic view of the viewing hood of the invention.

FIG. 26 is a perspective view of a porous net with an inserted electrode for use in the electrophoresis-electroblot-transilluminator unit of the invention.

DETAILED DESCRIPTION OF THE INVENTION AND PREFERRED EMBODIMENTS THEREOF

According to the objectives discussed above, the present invention provides an apparatus for performing multiple molecular analysis operations without disturbing the gel. The apparatus disclosed is adapted to cast a separation gel, run electrophoresis with UV detection and viewing ability, perform electroblotting, capillary blotting, vacuum blotting, electroelution, UV crosslinking and record the results photographically, while the gel remains in place.

Figure 1:
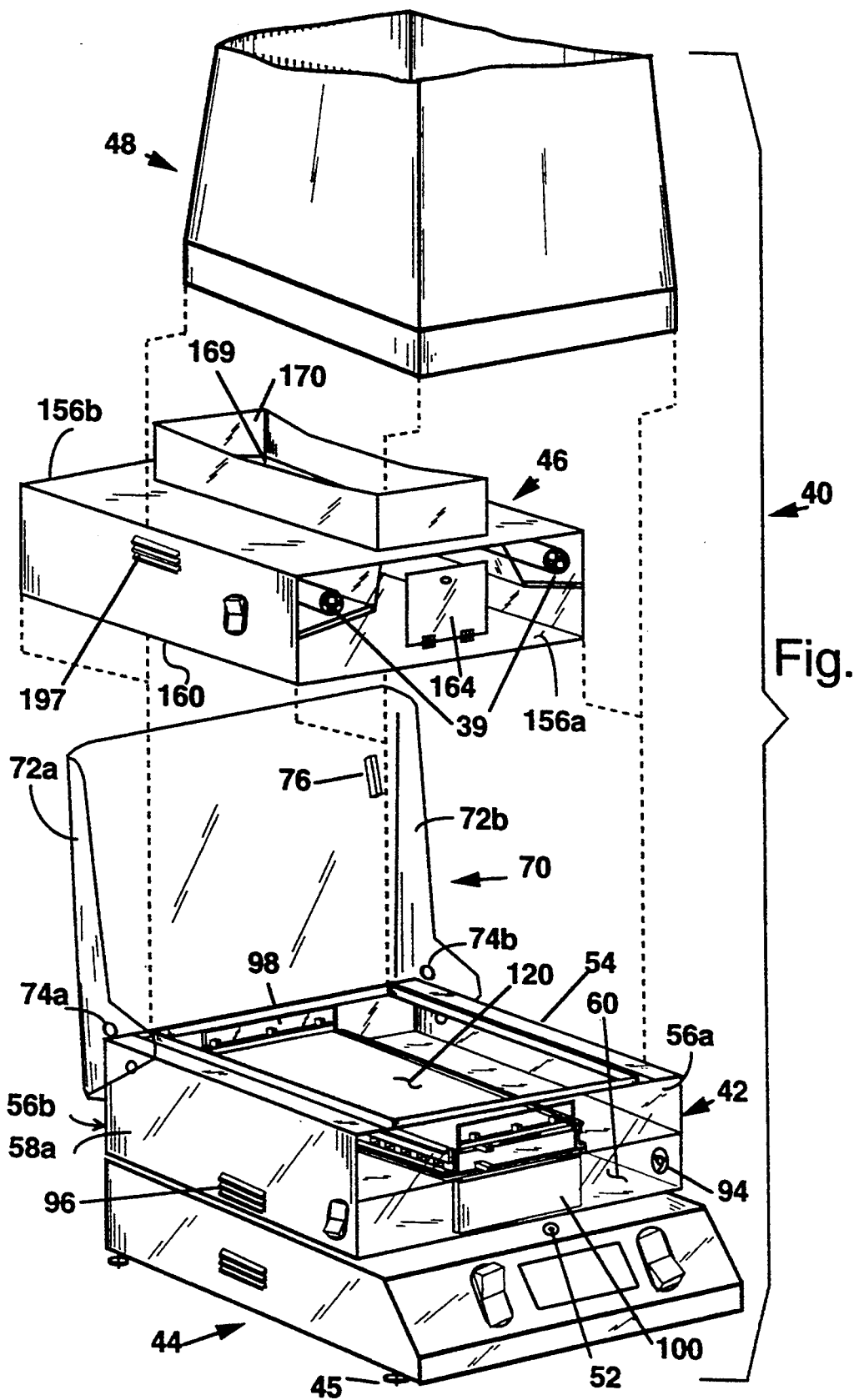
FIG. 1 is an exploded perspective view of a multipurpose electrophoresis apparatus made according to the invention and including a power source, an electrophoresis-electroblot unit, a viewing hood and a partial camera hood.

FIG. 1 is an exploded perspective view of the overall electrophoresis apparatus 40 of the invention, comprising a multi-purpose electrophoresis-electroblot-transilluminator unit 42 with a built-in UV radiation source, a power source 44, a viewing hood 46, and an attachable camera hood 48. Power source 44 supplies electrical power to multi-purpose electrophoresis-electroblot-transilluminator unit 42, UV radiation source, and viewing hood 46. A plurality of positioning knobs 50 (FIG. 5) protrude downwardly from the bottom surface of the UV transilluminator of the electrophoresis unit 42 and mate with a plurality of matching indentations (not shown) formed in the top surface of power source 44 for accurately locating mating electrophoresis unit 42 thereon. A plurality of adjustable leveling legs 45 are attached to the bottom surface of the housing of the power source 44 to provide optimum leveling and stabilization of electrophoresis-electroblot-transilluminator unit 42. A bubble level indicator 52 is also provided to verify the level.

Figure 4:
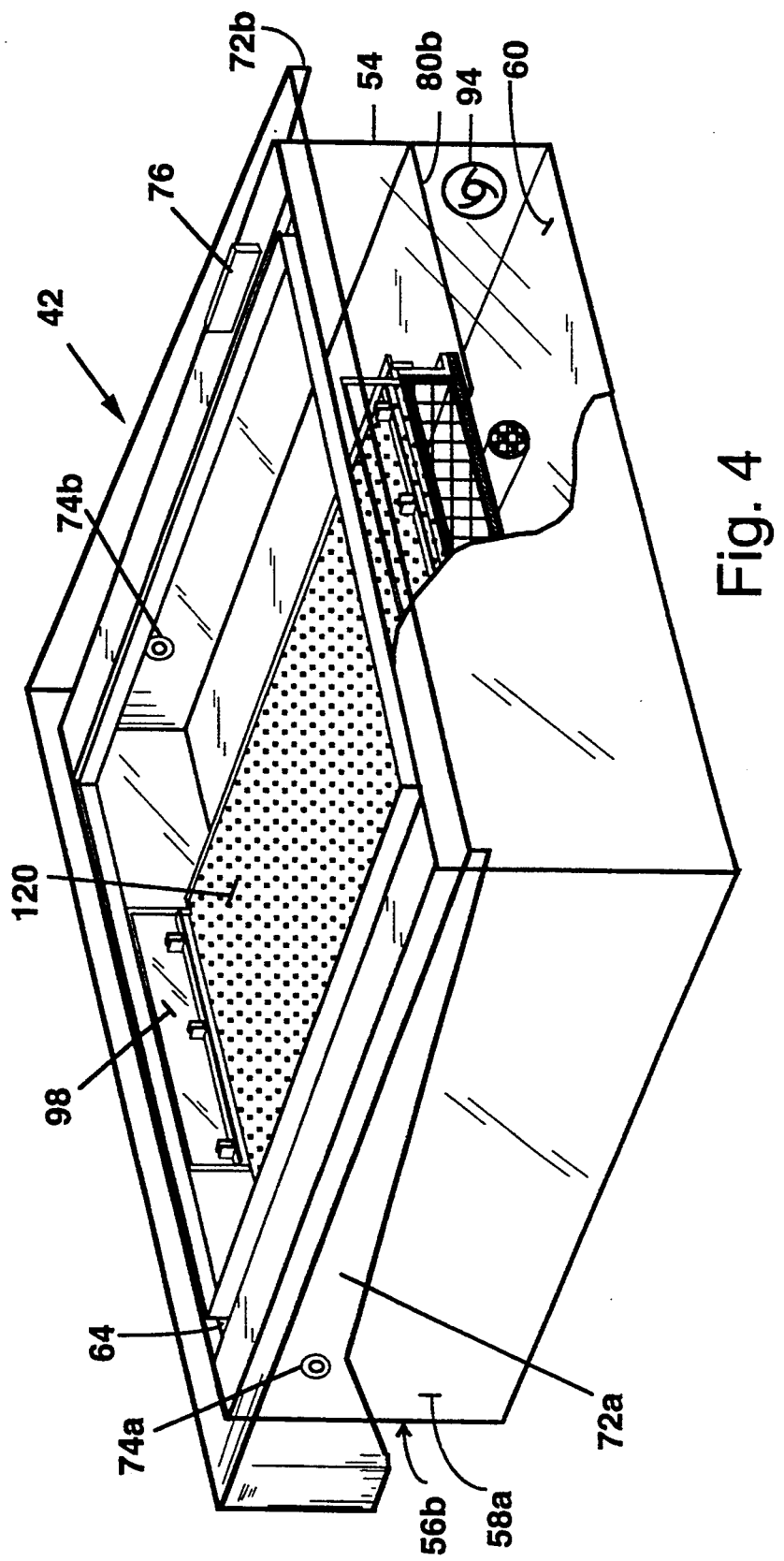
FIG. 4 is a perspective view of the electrophoresis-electroblot unit showing its safety cover in a closed position.
Figure 5:
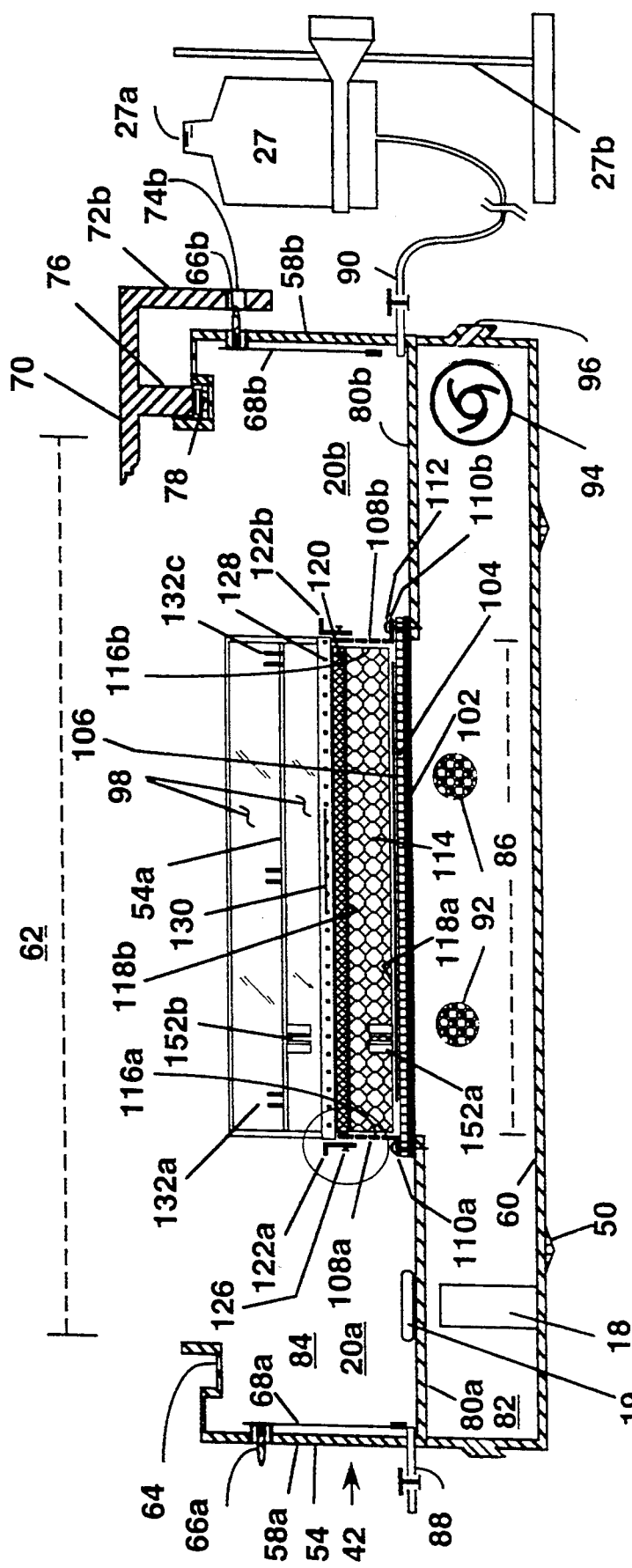
FIG. 5 is a front elevation schematic view of the electrophoresis-electroblot-transilluminator unit showing its slidable dams in their upper position for gel casting.

The electrophoresis-electroblot-transilluminator unit 42 as illustrated in detail in FIG. 5 includes an open topped container 54 having two end walls 56a, 56b, two side walls 58a, 58b, a substantially horizontal planar floor 60 and a grooved rim 64 circumscribing top opening 62. A pair of strip electrodes 68a, 68b are attached to the inside surface of side walls 58a, 58b respectively to terminate at a level adjacent partitions 80a, 80b. A first pair of electrical socket contacts 66a, 66b are mounted through side walls 58a, 58b and are connected to strip electrodes 68a, 68b. Socket contacts 66a, 66b are connectable to power source 44 by power cables (not shown). Cover 70, illustrated in FIGS. 1, 4 and 5 is hingedly attached to end wall 56b and includes downwardly extending flanges 72a, 72b. When cover 70 is closed, flanges 72a, 72b reside immediately adjacent and outwardly of the respective side walls 58a, 58b of electrophoresis-electroblot-transilluminator unit 42. Apertures 74a, 74b penetrate through flanges 72a, 72b respectively and are positioned to disclose socket electrodes 66a, 66b when cover 70 is closed. Protrusion 76 is located on the inside surface of cover 70 and makes contact with a normally open switch 78 located within peripheral groove rim 64 of container 54 when cover 70 is closed (FIGS. 4 and 5), closing switch 78 to complete an electrical circuit so as to provide electrical power to the electrophoresis-electroblot-transilluminator unit 42, UV radiation source and/or viewing hood 46 when cables are connected. Protrusion 76 and switch 78 provide a safety mechanism for cutting off electric power to the electrophoresis-electroblot-transilluminator unit 42 once cover 70 is opened, or when viewing hood 46 or camera hood 48 is removed.

As illustrated in FIGS. 4 and 5, substantially horizontal co-planar opposed partitions 80a, 80b are located intermediate floor 60 and top opening 62 and extend perpendicularly from the inside surfaces of side walls 58a, 58b and end walls 56a, 56b. Partitions 80a, 80b are separated by an open channel 86 and divide container 54 into lower chamber 82 and upper chamber 84. The container 54 and partitions 80a, 80b are made from opaque rigid plastic material of a type which is impenetrable by light and resistant to attack by the chemical solutions and materials to be placed therein.

Outlet valve 88 and inlet valve 90 penetrate through walls 58a and 58b respectively and are located slightly above partitions 80a and 80b for draining or filling upper chamber 84 with buffer when open channel 86 is sealed. A buffer reservoir 27 is slidingly mounted on clamp stand 27b and connected to inlet valve 90 such that the buffer solution is automatically added to upper chamber 84 when inlet valve 90 is open and outlet valve 88 is shut. The buffer reservoir 27 is raised or lowered along clamp stand 27b to achieve the buffer level desired. The screw cap of the buffer reservoir 27 has a built-in whistle 27a which sounds whenever buffer reservoir 27 is moved up or down. Inlet valve 90 is shut and outlet valve 88 is opened to drain upper chamber 84 of buffer.

Figure 2:
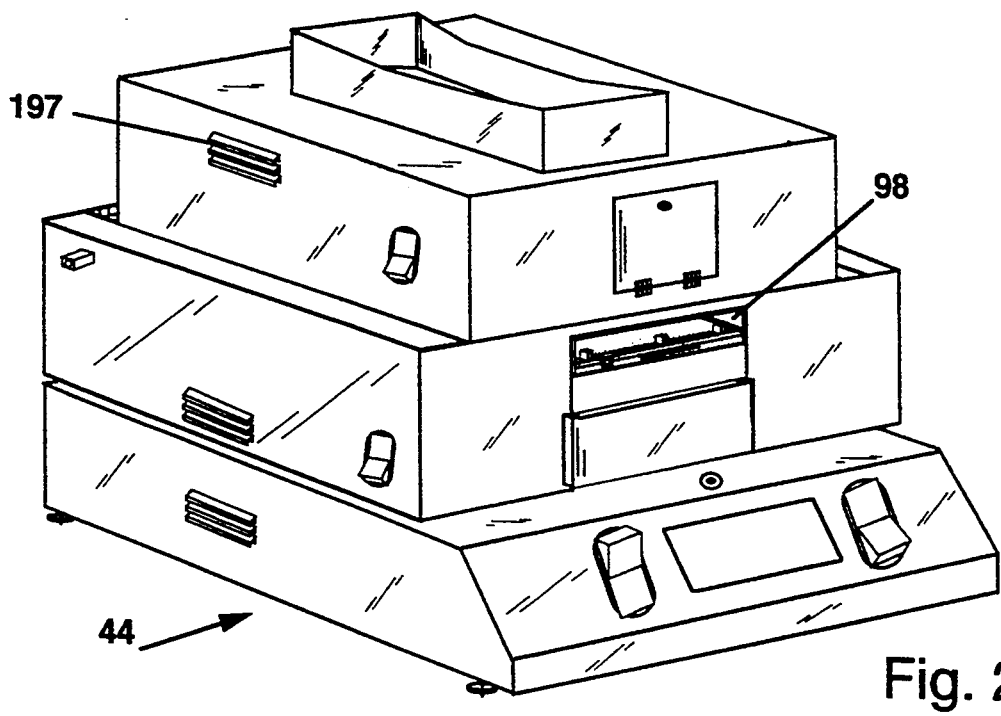
FIG. 2 is a perspective view of the multi-purpose electrophoresis apparatus of FIG. 1 showing the viewing hood mounted on the electrophoresis-electroblot-transilluminator unit.
Figure 3:
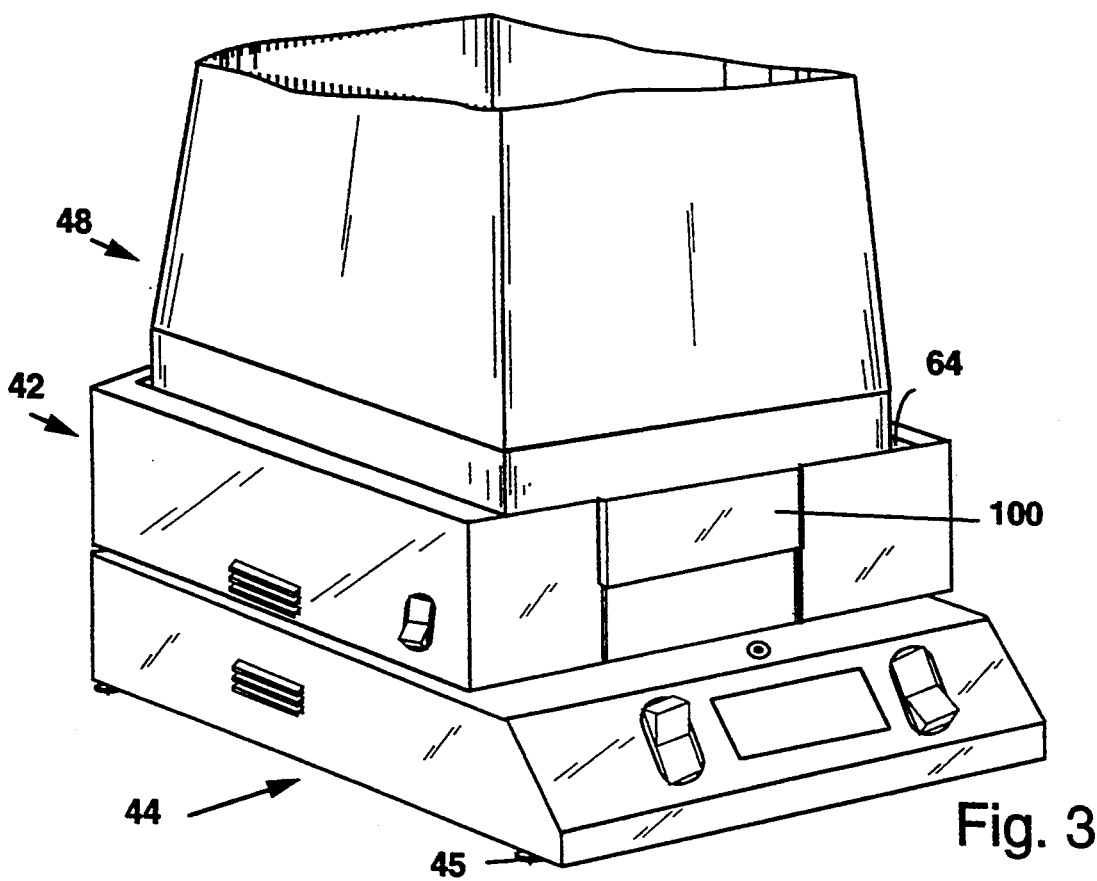
FIG. 3 is a perspective view of the multi-purpose electrophoresis apparatus showing placement of the camera hood mounted on the electrophoresis-electroblot unit.

A UV radiation source 92, able to emit at about 300 nm wavelength for observation of samples, is located in the lower chamber 82 directly beneath open channel 86 as shown in FIG. 5. An alternate embodiment is to position the 300 nm UV source above gel platform 120, in which case the structure below the gel does not need to be UV transparent. A cooling fan 94 is provided in the; lower chamber 82 for exhausting the heated air generated by UV source. Air exchange ducts 96 are provided in the lower chamber wall for admitting air into lower chamber 82. End walls 56a, 56b include UV blocking but visible light transparent viewing windows 98 which transmits visible light frequencies and blocks transmission of UV radiation frequencies, for safely viewing UV irradiated sample bands (FIGS. 2 and 5). Door 100, shown open in FIG. 1 and closed in FIG. 3, is slideably attached to the outside of container 54 and slides up to block ambient light from penetrating through viewing window 98 so as to provide a dark interior for photography of the UV irradiated gel.

As illustrated in FIG. 5, UV filter glass 102, capable of transmitting an optimum 300–312 nm frequency radiation, spans open channel 86. Protector glass 104 is superimposed upon UV filter glass 102 for physical protection thereof. An electrode 106 is permanently mounted or printed thereon and distributed across the upper surface of protector glass 104. Perforate walls 108a, 108b extend upwardly from protector glass 104 and are attached thereto by horizontally extending lower flanges 110a, 110b and fasteners 112. UV transparent spacer box 114 is insertable between porous walls 108a, 108b. Spacer box 114 comprises porous side supports 116a, 116b which function to interconnect porous bottom plate 118a and porous upper plate 118b. The porosity of spacer box 114, side supports 116a, 116b and plates 118a, 118b serves to permit full flow of buffer beneath gel casting platform 120. Gel casting platform 120 is permeable or impermeable according to different embodiments described below and is fixedly supported upon the porous upper plate 118b by convenient means. A plurality of fasteners 112 penetrate through flanges 110a, 110b, protector glass 104, UV filter glass 102 and partitions 80a, 80b for establishing an intimate sealing contact therebetween. The penetrability of walls 108a, 108b and spacer box 114 allow the buffer to reside directly beneath gel casting platform 120 and gel 128 supported thereon and to diffuse therethrough when a permeable gel casting platform 120 is used. Fasteners 112 are retractable to open channel 86 from above for replacement or repair of the UV radiation source units 92. UV filter glass 102, protector glass 104, spacer box 114 and gel casting platform 120 allow UV radiation to reach gel 128 from UV source 92 located below. A magnetic stirrer 18 housed in lower chamber 82 and a magnetic stirrer bar 19 placed in upper chamber 84 of electrophoresis unit 42 act to circulate the buffer solution in electrophoresis unit 42.

Referring to FIGS. 6 and 13, dams 122a, 122b are elongate, vertically oriented slats extending between end walls 56a, 56b and include vertical slots 124 for slidably mounting dams 122a, 122b on elongate fasteners 126 which are attached to side supports 116a, 116b. When dams 122a, 122b slide upwardly in close sealing contact with supports 116a, 116b as illustrated in FIGS. 5, 6, 7 and 13, their uppermost edges extend above the upper surface of gel casting platform 120 to hold a gel forming liquid (e.g. agarose) on gel casting platform 120 for hardening into gel 128. After gel 128 has formed, dams 122a, 122b are lowered beneath gel 128 (FIG. 8). By supplying a porous gel platform, the buffer solution totally surrounds the gel and the movement of molecular samples through the gel is more linear through the entire well depth.

As illustrated in FIG. 14, projections 130 are formed integral with the end walls 56a, 56b and are positioned slightly above gel casting platform 120. When gel 128 is cast on gel casting platform 120, the projections 130 engage cast gel 128 and prevent gel 128 from floating when a buffer solution is raised above the level of the gel platform 120. Platform 120 may be formed of imperforate plastic sheet for horizontal electrophoretic analysis, but is formed of a microporous sheet material in the preferred embodiment so as to enable vertical electrical field effect or vacuum blotting.

Also illustrated in FIG. 14, gel partition carriage 134, having lever release ends 136a, 136b, is removeably mounted between end walls 56a, 56b. Gel partition 135, having a bottom silicone pad 140 for softly contacting gel casting platform 120, is insertable into grooves 142a or 142b on the downwardly facing surface of gel partition carriage 134 for partitioning gel 128 along a line parallel to end walls 56a, 56b. Gel 128 may be thus divided into two substantially equal or unequal size gels respectively (shown in plan view in FIG. 16). Gel partition 135 contains vertical slots 137a, 137b penetrating therethrough for receiving comb 58 (FIG. 13).

As illustrated in FIG. 15, a series of comb receiving channels 132a, 132b, 132c, and 132d, 132e, 132f are attached to end walls 56a, and 56b respectively. Comb 58 (FIGS. 7 and 13), adapted for making wells in gel 128, during casting, is insertable into opposed comb slot sets 132a/13d, 132b/132e, or 132c/132f.

The multi-purpose electrophoresis apparatus 40 also provides a method for packing a molecular sample to the bottom of each formed well. A sample is loaded into a formed well. A vertical electric field is applied briefly to cause sample molecules to migrate to the bottom of the well, and then the vertical electric field is discontinued and immediately shifted to energize a horizontal field thereby compacting the sample molecules to one corner of the well. As a result of being compressed to the corner of each respective well, samples will migrate through the gel as a compact line, thus resulting in comparatively narrow, straight, well defined sample bands.

The apparatus 40 of the present invention is adapted to vertically transfer single bands or the entire sample contents of gel 128 to a suitable membrane 144 after the electrophoresis separation is complete. For transfer of the sample contents of the entire gel 128, as illustrated in FIG. 9, the buffer level is lowered to expose gel 128 by physically lowering the buffer container 27 (FIG. 5). A membrane 144 is superimposed upon entire gel 128. Absorbent Whatman paper sheet 146 is superimposed upon membrane 144. Porous net box 148 (shown in detail in FIG. 26) having electrode 150 distributed along its bottom interior surface, which is connectable to contact 152b (FIG. 5), through a ball connector 152d on the porous net 148, is superimposed upon Whatman paper 146. A second pair of terminals 151a and 151b are made to contact sockets 152a, 152b at end wall 56a, and are connected to electrode 106 and 150 respectively. Contacts 152a, 152b are connectable to a power source 44 by power cables. When the buffer level is raised above electrodes 106 and 150 and electrical power is applied, a vertical electric current is established therebetween. Viewing window 98 is provided to observe progress of electro-blot transfer to membrane 144.

Figure 23:
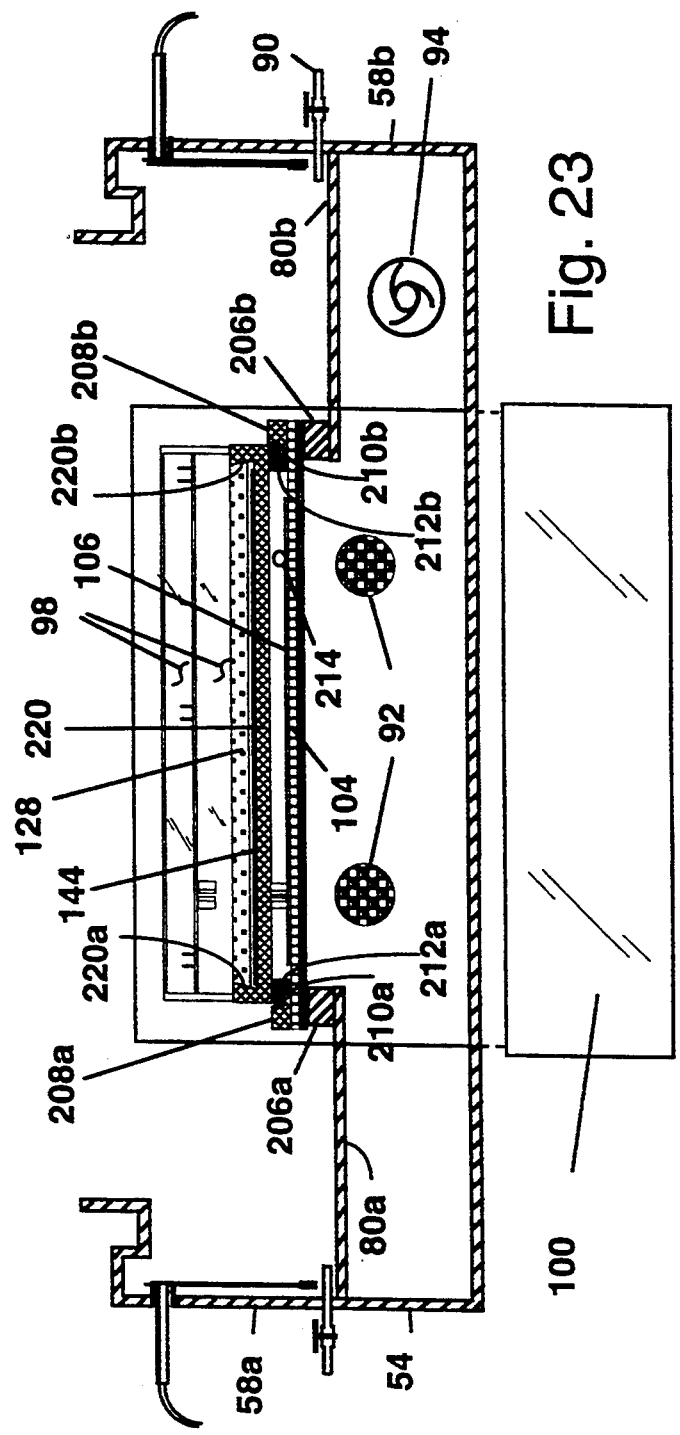
FIG. 23 is a side elevation schematic view of the electrophoresis-electroblot-transilluminator unit showing another embodiment with fixed dams adapted for vacuum blotting.

FIG. 23 portrays the electrophoresis unit of the invention in side view with vertically slideable door 100 positioned below container 54 for clarity. When mounted, door 100 is positioned as in FIG. 24 and may be moved upwardly to the position shown in FIG. 3 to obscure ambient light.

As illustrated in FIG. 25, viewing hood 46 includes a top opaque platform 154, two end walls 156a, 156b and two side walls 158a, 158b that extend downwardly to form a continuous lowermost edge 160 mateable with grooved rim 64 of electrophoresis-electroblot-transilluminator unit 42 (FIG. 5). Viewing hood 46 is operational during single sample band vertical electro-blot transfer of sample record to adjacent membrane 144. An electrical contact (not shown) is located on the bottom edge of viewing hood 46 to make contact with a source contact on container 54 to provide electrical power to viewing hood 46 when viewing hood 46 is mounted thereon. The viewing hood electrical contact (not shown) and switch 78, pressed by lower edge 160, provide a safety mechanism for cutting off electric power to electrophoresis-electroblot-transilluminatorting unit 42 once viewing hood 46 is removed from electrophoresis-electroblot-transilluminatorting unit 42. UV filter glasses 162a 162b for 254 mn wavelength, span opposed inside corners to encase a pair of 254 nm UV tubes 168 which are, operative for cross-linking of samples. Physically protective glass 163a, 163b is superimposed on the downwardly facing surface of each of UV filter glasses 162a, 162b respectively to protect filter glasses 162a, 162b from damage. Multiple air vents 197 are provided in the UV opaque body of viewing hood 46 for allowing air exchange during use.

Viewing hood 46, illustrated in FIG. 25, includes a door opening 164. Service door 166 is hingeably connected to an edge of door opening 164 and may swing to an open position. A normally open switching device known in the art (not shown) is located adjacent door opening 164 such that closed service door 166 causes the switch to be closed and power supplied to electrophoresis-electroblot-transilluminatorting unit 42 and viewing hood 46. When door 166 is open, electric power is cut off from electric sockets 66a, 66b, 152a, and 152b while supply of power to UV viewing radiation source 92 remains connected. A viewing frame 170 contains a UV blocking viewing window 169 which transmits visible light. Platform 154 and walls 156a, 154b, 158a, 158b are made of UV opaque, rigid plastic material of a type which is visible light impenetrable and resistant to attack by certain chemicals used in these processes. A UV radiation switch 20 is located on an exterior side surface of viewing hood 46 for activating UV radiation source 168.

For vertical single band electroblotting the buffer level is lowered to expose gel 128. The operator looks through UV viewing window 169 and selects a UV irradiated sample band for subsequent transfer to a membrane. A small piece of membrane 144 is cut and placed, with the help of a forceps operable through the service door 166 (FIG. 25), over the selected band. Membrane retainer 176 (FIGS. 12 and 17), having a thin rigid perforated sheet 178 and four piercing peripheral legs 180 extending perpendicularly, is inserted directly into the gel 128 and over the adjacent membrane 144 to press membrane 144 firmly against gel 128 and to prevent membrane 144 from floating once the buffer level is raised. Viewing hood 46 is removed and net 148 (FIG. 26) is positioned above membrane retainer 176, membrane 144 and gel 128. The cover 70 is closed. The buffer level is raised and electric power is supplied to electrodes 106 and 150 (FIG. 11) causing the selected sample band to transfer from gel 128 to adjacent membrane 144. Viewing window 98 provides for safe visual observation of vertical electroblotting. Electrophoretic separation of molecules within gel 128 and electroblotting transfer to membrane 144 may be accomplished and viewed alternatively by viewing hood mounted on electrophoresis-electroblot-transilluminator unit 42.

As illustrated in FIGS. 18 and 19, a second embodiment provides a hinged membrane holder 182 for vertical single band electroblotting. Membrane holder 182 includes a perforated lower member 184a hingedly connected to perforated upper member 184b. Cup 186 is integrally molded to upper surface of upper member 184b. Piercing legs 188 extend downwardly from the lower surface of lower member 184a. Lower member 184a and upper member 184b are snapped closed by snap 190 integral to lower member so as to securely hold membrane 144 placed therebetween. Viewing hood 46 is attached to electrophoresis-electroblot-transilluminator unit 42 (FIG. 2). Hinged membrane holder 182, is inserted directly into gel 128 upon a selected sample band in gel 128 with forceps operable through service door 166. Viewing hood 46 is removed and net 148 is positioned above hinged membrane holder 182 and gel 128. Cover 70 is closed, or viewing hood 146 is replaced, the buffer level is raised and electric power is supplied to sockets 152a, 152b causing the selected sample band to transfer from gel 128 to adjacent membrane 144. Viewing window 98 provides for safe visual observation of vertical electroblotting. Once transfer is complete, membrane holder 182 is removed. Cup 186 is configured to be insertable into a microfuge tube for further processing of sample molecules adsorbed on membrane 144 being held within holder 182. Washing and elution of sample molecules can be done by spinning the holder 182 and the microfuge tube together.

The multi-purpose electrophoresis apparatus 40 also provides a method for single band horizontal electroblotting, as illustrated in FIG. 10A. Membrane holder 192 (shown in detail in FIGS. 20 and 21) includes a perforated back member 194a hingeably connected to a perforated front member 194b, and a piercing insertion end 196. Membrane 144 is placed between back and front members 194a, 194b. Back member 194a and front member 194b are snapped closed by snap 198 integral to back member 194a so as to securely hold membrane 144 placed therebetween. Viewing hood 46 is attached to electrophoresis-electroblot-transilluminator unit 42 (FIG. 2). Insertion end 196, is firmly embedded into gel 128 directly in front of a selected sample band migration pathway with the help of forceps operable through service window 166. Membrane holder 192 is made of lightweight materials such that it remains vertical once inserted into gel 128. The service door 166 is closed and electric power reconnected to sockets 66a, 66b to cause transfer of the selected sample band to adjacent membrane 144. Viewing window 98 also provides for safe observation of single band horizontal electroblotting. Once transfer is complete, electric power is turned off and the membrane is retrieved for further processing.

The advantages associated with the process of electrotransfer as mentioned above in FIGS. 9, 10a and 11 is that one need not cut any gel piece out of the main gel 128 as is being done with currently known apparatus.

To cross-link a molecular sample to membrane 144 the buffer level is lowered to expose membrane 144. Viewing hood 46 is placed on electrophoresis unit 42. UV light tubes 168 mounted within viewing hood 46 are switched on for an appropriate time, for example, approximately ten minutes to accomplish UV crosslinking.

Figure 22:
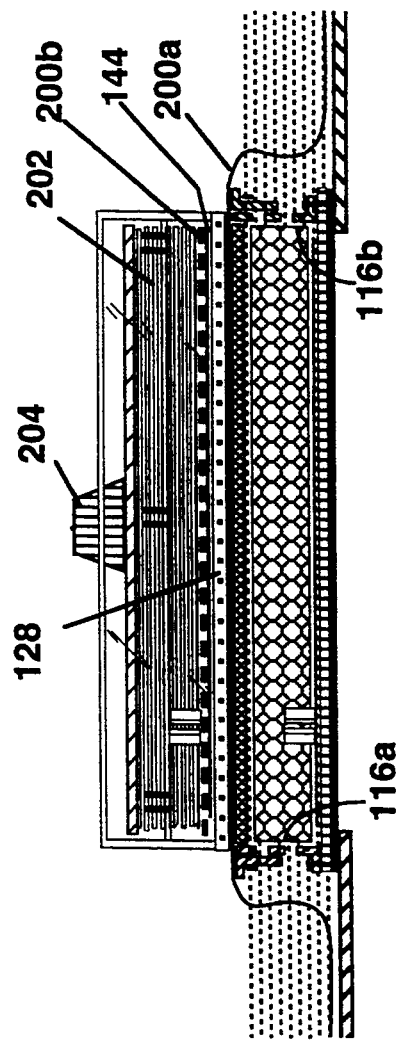
FIG. 22 is a front elevation schematic view of the upper chamber of the electrophoresis-electroblot-transilluminator unit shown in its capillary blotting mode.

As illustrated in FIG. 22, the electrophoresis apparatus 40 also provides a method for capillary blotting. Two sheets of Whatman paper 200a, 200b are used in this mode. Gel 128 is removed for denaturation and neutralization. Alternately, the gel is not removed, the buffer is replaced by a denaturing and neutralizing buffer; followed by replacement with a transfer buffer. A first layer of absorbent Whatman paper sheet 200a is placed across entire gel casting platform 120 of a length such that the end edges of the paper 200a drape into the buffer solution residing in the right and left sections of upper chamber 84 to act as a buffer wick. Gel 128 is superimposed upon Whatman paper sheet 200a in a position directly above gel casting platform 120. Suitable membrane 144 is superimposed upon gel 128. A second layer of Whatman paper 200b is superimposed upon membrane 144. A number of filter papers 202 are placed upon Whatman paper 200b. Weight 204 is placed upon a stack of filter papers 202. As buffer is absorbed upwardly through the layers, molecular sample bands transfer with the buffer from the gel 128 to adjacent membrane 144.

As illustrated in FIG. 23, a second embodiment provides an apparatus adapted for vacuum blotting. Horizontal partition walls 80a, 80b include upwardly extending edges 206a, 206b, upon which UV filter glass 102 and superimposed protector glass 104 are placed to extend therebetween. A pair of polymeric porous support spacers 208a, 208b having inwardly facing ledges 210a, 210b, are mounted upon protector glass 104 directly above edges 206a, 206b and extend between end walls 56a, 56b. Sealing gaskets 212a, 212b mate with protector glass 104 and porous support spacers 208a, 208b and extend from end walls 56a, 56b and are adapted to seal to modified gel casting platform 220 therebetween.

The gel casting platform 220 shown in FIGS. 23 and 24 is adapted to vacuum blotting techniques and operates in a unique fashion. Gel casting platform 220 is formed as a single piece of a microporous UV transparent material. Side walls 220a, 220b are integrally formed parts of platform 220 and are sloped inwardly at their respective tops, affording secure retention of gel 128 during all processing stages. This eliminates the need for moveable dams 122a and 122b (FIG. 5). The pores establish a path for buffer conducted electrical field transmission during electrophoresis or vacuum flow during vacuum blotting. The pores are sufficiently small to restrict the penetration of liquified gel.

Application of a vacuum by way of vacuum outlet vent 214 between gel casting platform 220 and protector glass 104 causes sample bands to migrate from gel 128 to underlying membrane 144. Progress of downward vertical transfer is safely observed through side viewing window 98 during UV irradiation of gel 128.

Another embodiment, as illustrated in FIG. 24, is adapted for electrophoresis and electroblotting. This embodiment is similar to the embodiment illustrated in FIG. 23, except that sealing gaskets 212a, 212b are not used, vacuum outlet 214 is shut off and buffer is capable of flowing through porous support spacers 208a, 208b to reside directly beneath gel casting platform 220. Thus, the embodiment illustrated in FIG. 24 executes methods and procedures as previously described for the principal embodiment.

Figure 27:
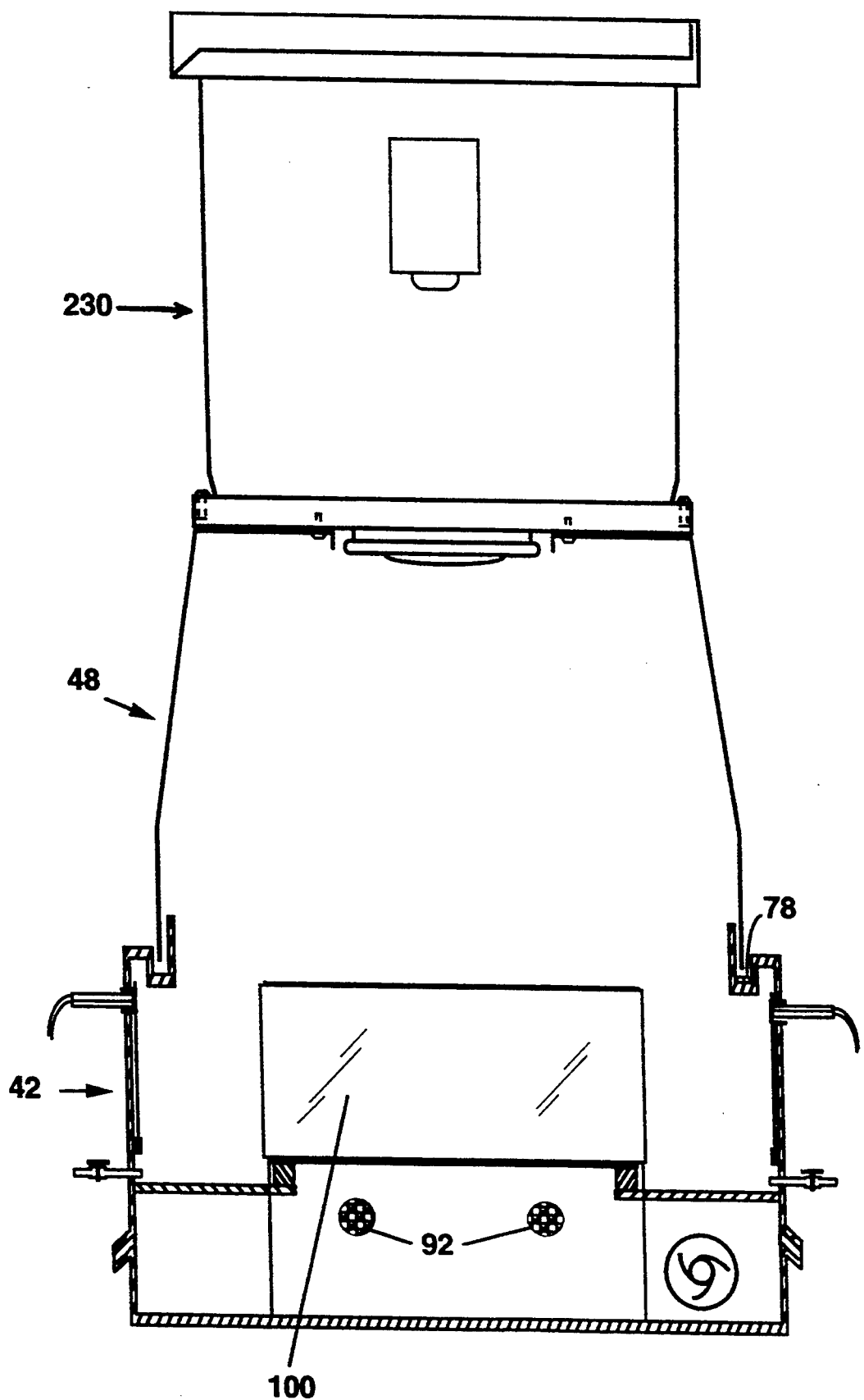
FIG. 27 is an elevation schematic view of the apparatus of the invention including a camera hood and a camera.

FIG. 27 shows camera hood 48 situated on top of electrophoresis-electroblot-transilluminator unit 42 so as to cause the normally open switch 78 to close and permit operation of the electrophoresis of the UV apparatus. A camera 230 is positioned to take photographs by the light emitted as the molecular sample in the gel and marked with ethidium bromide is caused to fluoresce under UV radiation. The walls of camera hood 48 are sloped to form a transition from the relatively small camera size to the larger size of electrophoresis-electroblot-transilluminator unit 42 and are opaque to visible light as well as UV radiation.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A multi-purpose apparatus for separation, transfer, visualization and recording of molecular samples in a gel, said apparatus comprising:
    (a) an open topped container having a planar floor;
    (b) a substantially rectangular planar gel casting platform mounted on a similarly sized porous spacer so that an upper surface of said platform resides horizontally within said container at a selected distance above said floor;
    (c) means positioned adjacent said platform in a manner to be moveable between a liquid retaining position for retaining a liquid on said platform which will harden to a gel and a retracted position;
    (d) a comb mountable within said container so as to reside proximately above said platform and adapted for forming a plurality of sample receiving wells into an upper surface of said gel;
    (e) means mounted within said container to establish a first electric field oriented parallel to and straddling said gel for separating said molecular samples into discrete bands;
    (f) a membrane superimposed upon said cast gel for reception of said bands transferred from said gel;
    (g) a porous net superimposed upon said membrane;
    (h) means mounted within said container so as to establish an alternate electric field vertically straddling said gel so as to cause the molecular sample to migrate vertically;
    (i) an UV radiation source mounted within said container in a position below said platform; and
    (j) a power source connectable to said electric field establishing means through a normally open switch mounted to said container.

2. A multi-purpose apparatus as recited in claim 1, further comprising a UV opaque cover attachable to said container so as to be moveable between an open and a closed position, and adapted to block UV radiation so as to allow safe viewing of said gel during UV irradiation and further adapted to cause said normally open switch to close.

3. A multi-purpose apparatus as recited in claim 1, further comprising a viewing hood removeably mountable on said container in a position over said open top, said hood being formed of UV and visible light blocking material and having a UV blocking, visible light transparent window formed therethrough for viewing of said gel during UV irradiation.

4. A multi-purpose apparatus as recited in claim 3, further comprising an opening formed in a side of said hood and adapted for accessing materials confined beneath said viewing hood when said viewing hood is mounted upon said container and a service door hingedly attached adjacent said opening such that said door is moveable between an open and a closed position of said opening.

5. A multi-purpose apparatus as recited in claim 3, wherein said viewing hood is adapted so as to close said normally open switch on said container.

6. A multi-purpose apparatus as recited in claim 3, further comprising a cross-linking UV radiation source mounted within said viewing hood and adapted for UV cross-linking of a molecular sample to said membrane and a means to energize and de-energize said cross-linking UV radiation source and an UV blocking material secured into said viewing hood in a position to enclose said UV radiation source.

7. A multi-purpose apparatus as recited in claim 1, wherein said container is made from a material capable of blocking visible light.

8. A multi-purpose apparatus as recited in claim 1, further comprising a pair of perforate walls extending vertically from said floor of said container in parallel, spaced apart orientation and forming a channel capable of receiving said spacer within said container.

9. A multi-purpose apparatus as recited in claim 1, wherein said means to retain said liquid upon said platform comprise a pair of dams, respectively vertically slidably attached to said vertically extending walls in a position so as to be moveable between an upper liquid retaining position and a lower retracted position.

10. A multi-purpose apparatus as recited in claim 1, further comprising a first porous membrane holder adapted to be operable in a horizontal orientation and including a plurality of piercing legs for insertion into said gel and a cup mounted directly above said held membrane, said membrane holder insertable into a microfuge tube for eluting a selected sample band from said membrane.

11. A multi-purpose apparatus as recited in claim 1, further comprising a second porous membrane holder having a pair of hingeably connected sides and adapted to be operable in a vertical orientation.

12. A multi-purpose apparatus as recited in claim 1, further comprising a membrane retainer insertable into said gel directly above a selected sample band for containing said gel and said membrane firmly between said gel and said retainer.

13. A multi-purpose apparatus as recited in claim 1, further comprising a plurality of protrusions formed integral with inner surfaces of said container above said gel casting platform for engaging and securing the position of said gel.

14. A multipurpose apparatus as recited in claim 1, wherein said platform is porous and a pair of opposed walls adjacent said platform are formed to slope inwardly so as to be closer together at their top edges than they are at their bottom edges so as to secure the position of said gel.

15. A multi-purpose apparatus as recited in claim 1, further comprising a gel partitioner mounted within said container and adapted to divide said gel along a line parallel to the direction of said first electrical field.

16. A multi-purpose apparatus as recited in claim 1, further comprising a camera hood mountable on said container and configured to receive a camera for photography of said gel located on said platform.

17. A multi-purpose apparatus as recited in claim 1, further comprising a viewing window formed from UV filtering material penetrating through a wall of said container.

18. A multi-purpose apparatus as recited in claim 16, further comprising a door moveable between a closed position in which said door covers the said viewing window and an open position in which said viewing window is uncovered.

19. A multi-purpose apparatus as recited in claim 1, further comprising a movable porous spacer box having porous upper and lower plates with interconnecting porous side walls adapted for mounting within said container.

20. A multi-purpose apparatus as recited in claim 1, wherein said container has an intake and an outlet for a liquid and further comprising liquid supply means adapted for maintaining said liquid at a selected level in said container.

21. A multi-purpose apparatus as recited in claim 1, wherein said gel casting platform is porous, is sealed peripherally to said container and spaced above said floor, and further comprising a vacuum source connected so as to be able to apply a vacuum beneath said gel casting platform so as to transfer a molecular sample from said gel to a membrane positioned beneath said gel.

22. A multi-purpose apparatus as recited in claim 1, further comprising means within said container for mechanically circulating a liquid in said container.

23. A multi-purpose apparatus for separation, transfer, visualization and recording of molecular samples in a gel, said apparatus comprising:

(a) an open topped container having a planar floor;

(b) a substantially rectangular planar gel casting platform mounted on a similarly sized porous spacer so that an upper surface of said platform resides horizontally within said container at a selected distance above said floor;

(c) means positioned adjacent said platform for retaining a liquid on said platform which will harden to a gel;

(d) a comb mountable within said container so as to reside proximately above said platform and adapted for forming a plurality of sample receiving wells into an upper surface of said gel;

(e) means mounted within said container to establish a first electric field oriented parallel to and straddling said gel for separating said molecular samples into discrete bands;

(f) a membrane superimposed upon said cast gel for reception of said bands transferred from said gel;

(g) a porous net superimposed upon said membrane;

(h) means mounted within said container so as to establish an alternate electric field vertically straddling said gel so as to cause the molecular sample to migrate vertically;

(i) an UV radiation source mounted within said container in a position below said platform; and (j) a power source connectable to said electric field establishing means through a normally open switch mounted to said container.

24. A multi-purpose apparatus for separation, transfer, visualization and recording of molecular samples in a gel, said apparatus comprising:

(a) an open topped container having a planar floor;

(b) a substantially rectangular planar gel, casting platform mounted on a similarly sized porous spacer so that an upper surface of said platform resides horizontally within said container at a selected distance above said floor;

(c) means positioned adjacent said platform in a manner to be moveable between a liquid retaining position for retaining a liquid on said platform which will harden to a gel;

(d) a comb mountable within said container so as to reside proximately above said platform and adapted for forming a plurality of sample receiving wells into an upper surface of said gel;

(e) means mounted within said container to establish a first electric field oriented parallel to and straddling said gel for separating said molecular samples into discrete bands;

(f) a membrane superimposed upon said cast gel for reception of said bands transferred from said gel;

(g) a porous net superimposed upon said membrane;

(h) means mounted within said container so as to establish an alternate electric field vertically straddling said gel so as to cause the molecular sample to migrate vertically;

(i) a power source connectable to said electric field establishing means through a normally open switch mounted to said container; and (j) a viewing hood removeably mountable on said container in a position over said open top, said hood being formed of UV and visible light blocking material and having a UV blocking, visible light transparent window formed therethrough for viewing of said gel during UV irradiation and including means to generate UV radiation for viewing said molecular samples and for cross-linking said molecular samples.

* * * * *